United States Patent [19]

Fox, Jr., deceased et al.

[11] Patent Number: 5,374,432
[45] Date of Patent: Dec. 20, 1994

[54] TOPICAL ANT-INFECTIVE OINTMENT CONTAINING SILVER OR SILVER SALTS AND ANTIBIOTICS

[75] Inventors: Charles L. Fox, Jr., deceased; by Alan F. Ruf, legal representative, both of Fort Lauderdale, Fla.; Shanta M. Modak, River Edge, N.J.

[73] Assignee: The Trustees of Columbia University of the City of New York, New York, N.Y.

[21] Appl. No.: 387,211

[22] Filed: Jul. 28, 1989

[51] Int. Cl.⁵ .............................................. A61K 33/38
[52] U.S. Cl. ................................. 424/618; 514/184; 514/252
[58] Field of Search ................ 424/618; 514/184, 252

[56] References Cited

U.S. PATENT DOCUMENTS

| | | | |
|---|---|---|---|
| 3,761,590 | 9/1973 | Fox | 424/228 |
| 4,347,238 | 8/1982 | Hollingsbee | 424/81 |
| 4,404,197 | 9/1983 | Fox et al. | 424/229 |
| 4,535,078 | 8/1985 | Fox, Jr. et al. | 514/157 |
| 4,563,485 | 1/1986 | Fox et al. | 523/113 |
| 4,612,337 | 9/1986 | Fox et al. | 523/113 |

OTHER PUBLICATIONS

Avery's Drug Treatment 3rd Ed Williams & Wilkins Baltimore MD.
Holder et al CA:106 #47128u 1987.
Darrell et al., Cornea 5 (4): 205–209 (1986).
Jacobson et al., Antimicrobial Agents and Chemotherapy 32 (12): 1820–1824 (1988).
Tokumaru et al., Res. Commun. Chemical Pathology and Pharmacology 8 (1): 151–158 (1974).
Mohan et al., Brit. J. Ophthamology 72: 192–195 (1988).
Darrell et al., Tr. Am. Opth. Soc. 82: 75–91 (1984).
Mohan et al., Indian J. Med. Res. 85: 572–575 (1987).
Gufic Ltd. Brochure on "SSZ" 1988.
Modak and Fox, "Sulfadiazine Silver-Resistant *Pseudomonas* in Burns", Arch. Surg., 116:854–857 (Jul., 1981).

*Primary Examiner*—Marianne M. Cintins
*Assistant Examiner*—Russell Travers
*Attorney, Agent, or Firm*—Brumbaugh, Graves, Donohue & Raymond

[57] ABSTRACT

Topical compositions for use in the treatment of burns and other infection-prone wounds and of ocular infection are provided. These compositions comprise silver or a silver salt, an antibiotic selected from among aminoglycoside antibiotics and quinolone antibiotics, with the proviso that the antibiotic is not norfloxacin; and a sterile carrier, such as water or an ointment base.

3 Claims, No Drawings

TOPICAL ANT-INFECTIVE OINTMENT CONTAINING SILVER OR SILVER SALTS AND ANTIBIOTICS

BACKGROUND OF THE INVENTION

This application relates to topical anti-infective ointments, particularly for use in the treatment of burns.

It is well established that microbial infection is one of the major complications associated with burn wounds, and that in the case of major burns this infection can lead to the death of the victim. Such infections can be caused by any of a number or organisms, although *Pseudomonas aeruginosa* is probably the most common.

To prevent or reduce infection of burn wounds, topical ointments have been used. These ointments have incorporated silver sulfadiazine (U.S. Pat. No. 3,761,590, incorporated herein by reference) or various antibiotics. A topical ointment for burns has also been reported which contains a combination of silver salts and norfloxocin, a quinoline antibiotic, or its salts (U.S. Pat. No. 4,404,197, incorporated hereby by reference). In the case where the antibiotic is silver norfloxocin, U.S. Pat. No. 4,404,197 reports a synergistic enhancement of activity.

In addition to efficacy, a significant concern in the treatment of burn wounds is the avoidance of resistant strains during prolonged treatment. We have now found that combinations of silver or silver salts with a variety of antibiotics not only provide improved antimicrobial efficacy, they also reduce the incidence of microbial resistance.

SUMMARY OF THE INVENTION

The present invention provides topical compositions for use in the treatment of burns and other infection-prone wounds and of ocular infection. These compositions comprise (a) silver or a silver salt, (b) an antibiotic selected from among cephalosporin, β-lactam antibiotics, aminoglycoside antibiotics and quinolone antibiotics, with the proviso that the antibiotic is not norfloxacin; and (c) a sterile carrier, such as water or an ointment base.

DETAILED DESCRIPTION OF THE INVENTION

The compositions of the invention comprise at least one antibiotic component, and at least one silver component different from the antibiotic component combined in an ophthalmic carrier.

The antibiotic component of the invention may be any antibiotic which is found suitable for use in topical ocular applications. Examples of suitable antibiotics include quinolone antibiotics such as norfloxacin (NF), pefloxacin (PF), ofloxacin (OF) and salts thereof; aminoglycosidic antibiotics such as tobramycin;, and cephalosporins such as ceftazidime (Fortaz®) and β-lactams such as pipracil and aztneonam.

The silver component of the invention may be elemental silver or a silver salt. Suitable silver salts include silver acetate, silver benzoate, silver carbonate, silver iodate, silver iodide, silver lactate, silver laurate, silver nitrate, silver oxide, silver palmitate, silver protein and silver sulfadiazine. The preferred compound for use as the silver component is silver sulfadiazine (AgSD).

The antibiotic component and the silver component are combined in the compositions of the invention in amounts which are effective to treat external ocular infections. In general, the antibiotic component will be incorporated in amounts of from about 0.1% to 2% by weight, preferably 0.5%, and the silver component will be incorporated in amounts of from about 0.1% to 2% by weight, preferably 0.5% to 1%.

Suitable carriers include sterile water, sterile saline and sterile ointment bases. Oil-in-water emulsions such as those disclosed in U.S. Pat. No. 4,347,238, incorporated herein by reference, may also be used.

The compositions of the invention provide a number of desirable properties which make them particularly suitable for use in the treatment of burn wounds. For example, AgSD is effective against a number of fungi associated with ocular keratomycosis, e.g., Aspergillus, Fusarium, Candida, Phycomyces and Allscheria and has been tested for use in ocular therapy with no toxic effects being observed. (Mohan et al., "Silver sulphadiazine in the treatment of mycotic keratitis", Indian J. Med. Res. 85, 572–575 (1987).) AgSD has also been shown to be effective against HSV and VSV in an ocular infection model. (Tokumaru et al., "Antiviral Activities of Silver Sulfadiazine in Ocular Infection", Res. Commun. Chem. Path. & Pharmacol. 8, 151–158 (1974). Silver sulfadiazine is also effective against many strains of *Ps. aeruginosa, S. aureus* and other bacteria. Thus, AgSD is effective against many of the organisms which present severe challenges to antibiotic therapy.

The compositions of the invention do not merely provide improved antimicrobial spectrum, however, but also exhibit synergistic enhancement of efficacy such that lower levels of the antimicrobial agent can be employed. This reduces the risk of irritation and other side effects of administration of the therapeutic agent. Further, the compositions of the invention actually exhibit a reduced tendency toward the development of drug-resistant strains, even in the case of quinolone antibiotics such as norfloxacin which are generally considered to have a low risk of resistance development.

Various aspects and advantages of the inventions are illustrated in the examples hereinbelow. These examples are provided for illustration only and are not intended to limit the invention.

EXAMPLE I

The efficacy of compositions of the invention for treating rabbit corneal ulcers caused by *Pseudomonas aeruginosa* was compared with that of two known antibiotics, tobramycin and norfloxacin, both of which have been used previously in treatment of such infections, using the same protocol described in Darrell et al., "Norfloxacin and Silver Norfloxacin in the Treatment of Pseudomonas Corneal Ulcer in the Rabbit", J. Tr. Amer. Ophth. Soc. 82, 75–91 (1984). The antimicrobial agents were applied as suspensions in sterile water beginning on day 1 after corneal inoculation with *Pseudomonas aeruginosa* and 4 times daily (every three hours) for four days thereafter using one of the 6 treatment regimes shown in Table I. Each treatment group consisted of 2 rabbits treated in both eyes.

Each test rabbit was monitored for corneal damage index (CDI) at intervals following the initial treatment with the antimicrobial agent. The CDI is the product of the percent of surface of the cornea which is ulcerated and the density of the corneal opacity relative to an unulcerated cornea. The observed data is reported in Table I.

As can be seen from this data AgSD, Tobramycin and NF are each effective to some degree against Pseudomonas infection, but combinations of AgSD and one of the antibiotics are superior. This is true even in the case where the level of NF is reduced by 50%, even though AgSD alone merely retarded the infection and was not effective to reduce the damage.

TABLE I

Topical Therapy of Rabbit Corneal Ulcers Due to Ps. aeruginosa Infection

| Treatment Group | Corneal Damage Index (Days) | | | | |
|---|---|---|---|---|---|
| | 0 | 1 | 2 | 3 | 6 |
| Untreated (Control) | 60 | 240 | 300 | 270 | 300 |
| 1% Silver Sulfadiazine | 60 | 90 | 180 | 150 | 120 |
| 1% Tobramycin | 50 | 70 | 75 | 70 | 70 |
| 1% Norfloxacin | 75 | 80 | 45 | 45 | 45 |
| 1% Silver Sulfadiazine + 1% Tobramycin | 60 | 50 | 45 | 45 | 45 |
| 1% Silver Sulfadiazine + 0.5% norfloxacin | 60 | 60 | 30 | 30 | 30 |

EXAMPLE II

This improvement is performance for the combination of the invention was shown further in an experiment to test the effect of various levels of tobramycin and AgSD against mixed cultures of *Pseudomonas aeruginosa* and *Staphylococcus aureus*.

Method of Testing Synergistic Activity In Vitro 5 ml trypticase soy broth containing different amounts of the drugs was inoculated with 0.1 ml of either mixed culture of equal amounts of *Ps. aeruginosa* and *Staph. aureus* ($10^4$ organisms) or single cultures. The tubes were incubated at 37° C. and after 24 hours they were observed for turbidity (bacterial growth). Visible bacterial growth was rated according to the optical density of turbidity (+ being light turbidity and ++++ heavy turbidity).

The results of this experiment are shown in Table II. As shown, combinations of AgSD and tobramycin at levels which are insufficient to prevent bacterial growth used separately are effective when used in combination. Similar results were observed for individual cultures of *Ps. aeruginosa* and *S. aureus* as shown in Table III and IV.

TABLE II

Synergistic Action of AgSD and Tobramycin against Mixed Cultures of Ps. aeruginosa and Staph., aureus

| Compounds | Concentration of Drug (nanomole/ml) | | | |
|---|---|---|---|---|
| Silver Sulfadiazine | 100 | 50 | 25 | 12.5 |
| Growth | + | +++ | ++++ | ++++ |
| Tobramycin | 20 | 10 | 5 | 2.5 |
| Growth | ++ | ++++ | ++++ | +++ |
| Silver Sulfadiazine + | 50 | 25 | 12.5 | 6.25 |
| Tobramycin | 10 | 5 | 2.5 | 1.25 |
| Growth | 0 | 0 | ++ | ++ |

+ visible light bacterial growth
++++ heavy bacterial growth
0 no bacterial growth

TABLE III

Antibacterial Efficacy of Sulfadiazine, Silver Sulfadiazine and Tobramycin against Ps. aeruginosa

| Compounds | Concentration of Drug (nanomole/ml) | | | | |
|---|---|---|---|---|---|
| Silver Sulfadiazine | 200 | 100 | 50 | 25 | 12.5 |
| Growth | 0 | + | +++ | ++++ | ++++ |
| Tobramycin | 200 | 100 | 50 | 25 | 12.5 |
| Growth | 0 | 0 | 0 | ++ | ++++ |
| Silver Sulfadiazine + | 100 | 50 | 25 | 12.5 | 6.25 |
| Tobramycin | 25 | 25 | 25 | 25 | 25 |
| Growth | 0 | 0 | 0 | 0 | 0 |
| Sulfadiazine | 200 | 100 | 50 | 50 | 12.5 |
| Growth | ++++ | ++++ | ++++ | ++++ | ++++ |
| Tobramycin | 200 | 100 | 50 | 25 | 12.5 |
| Growth | 0 | 0 | 0 | ++ | ++++ |
| Sulfadiazine + | 200 | 100 | 50 | 25 | |
| Tobramycin | 25 | 25 | 25 | 25 | |
| Growth | ++++ | ++++ | ++++ | ++++ | |

TABLE IV

Synergistic Antibacterial Efficacy of Silver Sulfadiazine and Tobramycin against Staph. aureus

| Compounds | Concentration of Drug (nanomole/ml) | | | | |
|---|---|---|---|---|---|
| Silver Sulfadiazine | 200 | 100 | 50 | 25 | 12.5 |
| Growth | 0 | + | ++ | ++++ | ++++ |
| Tobramycin | 200 | 100 | 50 | 25 | 12.5 |
| Growth | 0 | 0 | 0 | ++ | ++++ |
| Silver Sulfadiazine + | 100 | 50 | 25 | 12.5 | |
| Tobramycin | 25 | 25 | 25 | 25 | |
| Growth | 0 | 0 | 0 | 0 | |

+ visible light bacterial growth
++++ heavy bacterial growth
0 no bacterial growth

EXAMPLE III

The enhanced performance of combinations of silver sulfadiazine and other antibiotics against *Ps. aeruginosa* was demonstrated in burns.

Method of Testing Synergistic Activity in Vivo

Mice (female Swiss, 18 to 22 g) received nonlethal 30% scalds. The wounds were contaminated one hour after burn with freshly prepared 18 to 20 hour broth cultured of Pseudomonas (181) diluted to optical density 0.30. Infection in mice was induced by immersing the tail in the culture.

The first treatment was administered four hours after infection by rubbing the medicated creams over all burned surfaces. All drugs used were mixed in the cream base used for 1% sulfadiazine silver. Thereafter, all animals were observed and treated once daily; the primary criterion was survival. Animals that died underwent autopsy and cultures were made of the cardiac blood to verify the presence of Pseudomonas (181).

The results of this study are shown in Table V. These results show that while AgSD itself did not reduce mortality due to the infection its use in combination with an antibiotic resulted in further reductions in mortality when compared with the antibiotic alone.

TABLE V-A

In Vivo Synergism of Silver Sulphadizine and Antibiotics
(Topical Therapy of Burned Infected Mice)

| Group | (% mortality (Days Post Burn) | | | |
|---|---|---|---|---|
| | 2 | 4 | 6 | 8 |
| Untreated (Control) | 20 | 60 | 100 | 100 |
| 15mM AgSD | 40 | 80 | 100 | 100 |
| 10mM NF | 7 | 21 | 23 | 23 |
| 10mM NF + 15mM AgSD | 0 | 3 | 7 | 7 |
| 10mM PF | 9 | 11 | 29 | 37 |
| 10mM PF + 15mM AgSD | 0 | 9 | 11 | 11 |
| 10mM Enox | 0 | 5 | 50 | 50 |
| 10mM Enox + 15mM AgSD | 5 | 10 | 20 | 25 |
| 30mM ATN | 7 | 14 | 23 | 23 |
| 30mM ATN + 15mM AgSD | 0 | 7 | 13 | 17 |
| 10mM AgNF | 20 | 50 | 50 | 50 |
| 10mM AgNF + 30mM AgSD | 0 | 0 | 20 | 40 |
| 10mM NF + 30mM AgSD | 0 | 0 | 0 | 10 |
| 30mM AgSD | 0 | 80 | 100 | 100 |

(Burned mice are infected with Ps. aeruginosa [181] (sulfadiazine resistant strain)]).

TABLE V-B

Topical Therapy of Burned Mice
Infected with Ps. aeruginosa (sensitive strain)
(First treatment 4 hours post infection)

| Group | No. of Mice | % Mortality (Days Postburn) | | | |
|---|---|---|---|---|---|
| | | 2 | 4 | 6 | 8 |
| CONTROL | 20 | 20 | 80 | 100 | 100 |
| 30mM AgSD | 20 | 0 | 0 | 0 | 0 |
| 10mM AgSD | 25 | 60 | 75 | 75 | 75 |
| 5mM NF | 10 | 0 | 20 | 50 | 50 |
| 5mM NF + 10mM AgSD | 10 | 0 | 0 | 0 | 0 |
| 5mM PF | 10 | 0 | 40 | 60 | 60 |
| 5mM PF + 10mM AgSD | 10 | 0 | 0 | 0 | 0 |
| 15mM ATN | 25 | 0 | 20 | 30 | 40 |
| 15mM ATN + 10mM AgSD | 25 | 0 | 0 | 10 | 10 |

TABLE V-C (First treatment 24 hours post infection)

| CONTROL | 20 | 40 | 60 | 100 | 100 |
|---|---|---|---|---|---|
| 15-30mM AgSD | 20 | 20 | 40 | 60 | 60 |
| 10mM NF | 20 | 20 | 40 | 40 | 45 |
| 10mM NF + 15-30mM AgSD | 20 | 5 | 10 | 10 | 10 |
| 10mM PF | 20 | 25 | 50 | 60 | 65 |
| 10mM PF + 15-30mM AgSD | 20 | 10 | 25 | 25 | 25 |

TABLE V-C-continued (First treatment 24 hours post infection)

AgSD = Silver sulfadizine
NF = Norfloxacin
Enox = Enoxacin
PF = Pefloxacin
ATN = Aztreonam
AgNF = Silver norfloxacin

EXAMPLE IV

The degree to which resistant strains of microorganisms are induced by exposure to sub-inhibitory dosages of AgSD and various quinolone antibiotics was tested as shown in Table VI. As can be seen, there was little change in the susceptibility to AgSD through 10 passes at sub-inhibitory concentrations. Each of the antibiotics tested, however, became less effective after the ten passes by factors of 40 or more. Significantly, the extent of the reduction in efficacy was markedly decreased in each case when the quinolone antibiotic was used in combination with AgSD. This surprising result, combined with their combined spectrum of antimicrobial activity makes combinations of AgSD and quinolones unusually well suited for use in treatment of external ocular infections.

TABLE VI

Altered Susceptibility of Ps. aeruginosa
to Drugs after 10 Passages through
Sub-Inhibitory Concentrations

| Drugs | MIC (nmol/mL) | | Decrease Susceptibility |
|---|---|---|---|
| | Before Passage | After 10 Passages | |
| AgSD | 50.0 | 80 | 1.6 Fold |
| NF | 5.0 | 200 | 40.0 Fold |
| NF + AgSD | 7.5 | 75 | 10.0 Fold |
| PF | 5.0 | 200 | 40.0 Fold |
| PF + AgSD | 7.5 | 75 | 10.0 Fold |
| OF | 5.0 | 500 | 100.0 Fold |
| OF + AgSD | 3.0 | 50 | 16.7 Fold |
| DJ6783 | 6.0 | 250 | 41.7 Fold |
| DJ6783 + AgSD | 15.0 | 100 | 6.6 Fold |
| Fortaz | 1.5 | 200 | 133.0 Fold |
| Fortaz + AgSD | 12.0 | 100 | 8.3 Fold |

Ratio of antibiotic to AgSD is 1:2.
AgSD = Silver Sulfadiazine
NF = Norfloxacin
OF = Ofoxacin
PF = Pefloxacin

We claim:
1. An antiinfective composition for treatment of topical microbial infections comprising:
   (a) an effective amount of an antibiotic selected from the group consisting of aminoglycoside antibiotics and quinoline antibiotics with the proviso that the antibiotic is not norfloxacin;
   (b) an effective amount of silver or a silver salt selected from the group consisting of silver acetate, silver benzoate, silver carbonate, silver iodate, silver iodide, silver lactate, silver laurate, silver nitrate, silver oxide, silver palmitate, silver protein, and silver sulfadiazine; and
   (c) a sterile carrier, wherein the silver or silver salt and the antibiotic are present in amounts which are synergistically effective against infection.
2. A composition according to claim 1, wherein the silver or silver salt is present in an amount from 0.1% to 2% by weight and the antibiotic is present in an amount from 0.1% to 2% by weight.
3. A composition according to claim 1, wherein the antibiotic is a quinolone.

* * * * *